(12) United States Patent
Ganesan et al.

(10) Patent No.: US 7,329,720 B2
(45) Date of Patent: Feb. 12, 2008

(54) METHODS FOR INCREASING THE MEAN PARTICLE SIZE OF 2-HYDROCARBYL-3,3-BIS(HYDROXYARYL)PHTHALIMIDINES

(75) Inventors: Balakrishnan Ganesan, Karnataka (IN); Pradeep Jeevaji Nadkarni, Karnataka (IN)

(73) Assignee: General Electric Company, Schenectady, NY (US)

( * ) Notice: Subject to any disclaimer, the term of this patent is extended or adjusted under 35 U.S.C. 154(b) by 161 days.

(21) Appl. No.: 11/288,912

(22) Filed: Nov. 29, 2005

(65) Prior Publication Data

US 2007/0123712 A1    May 31, 2007

(51) Int. Cl.
*C08G 63/12* (2006.01)

(52) U.S. Cl. .................. 528/296; 264/14; 264/15; 544/144; 544/200; 548/472; 548/476

(58) Field of Classification Search ............... 264/14, 264/15; 528/296; 544/144, 200; 548/472, 548/476

See application file for complete search history.

(56) References Cited

U.S. PATENT DOCUMENTS

| 5,344,910 | A | 9/1994 | Sybert ............... 528/201 |
| 5,387,629 | A | 2/1995 | McGrath et al. |
| 5,455,310 | A | 10/1995 | Hoover et al. ............... 525/431 |
| 6,528,546 | B2 * | 3/2003 | Lee et al. .................. 521/48 |
| 2003/0181768 | A1 | 9/2003 | O'Young et al. ............ 568/728 |
| 2005/0075520 | A1 | 4/2005 | O'Young et al. ............ 568/728 |

FOREIGN PATENT DOCUMENTS

| EP | 0564233 A1 | 10/1993 |
| EP | 1582549 A1 | 10/2005 |
| GB | 1158606 | 7/1969 |
| GB | 1196871 | 7/1970 |
| JP | 03-070790 | 3/1991 |
| JP | 06-003838 | 1/1994 |
| JP | 06-082624 | 3/1994 |
| JP | 2005-206834 A | 4/2005 |

OTHER PUBLICATIONS

M.S. Lin et al., "Polymers With Improved Flammability Characteristics. I. Phenolphthalein-Related Homopolymers"; Journal of Polymer Science: Polymer Chemistry Edition, vol. 19, 2659-2670 (1981).

M.S. Lin et al., "Thermal Degradation Study of Phenolphthalein Polycarbonate", Journal of Polymer Science: Polymer Chemistry Edition, vol. 19, 2773-2797 (1981).

International Search Report; International Application No. PCT/US2006/045506; Date of Mailing: May 25, 2007.

Written Opinion; International Application No. PCT/US2006/045506; Date of Mailing: May 25, 2007.

Adamczyk Maciej et al "A Practical Method For The Synthesis Of Phenophthalein Spirolactams" Organic Preparations And Procedures International, vol. 33, No. 1, 2001, pp. 95-100.

* cited by examiner

*Primary Examiner*—Terressa Boykin

(57) ABSTRACT

A method for increasing a mean particle size of a 2-hydrocarbyl-3,3-bis(hydroxyaryl)phthalimidine is provided. The method comprises forming a mixture comprising a feedstream of the 2-hydrocarbyl-3,3-bis(4-hydroxyaryl)phthalimidine, and a solvent composition comprising an organic solvent and water, wherein the organic solvent is capable of at least partially dissolving the 2-hydrocarbyl-3,3-bis(hydroxyaryl)phthalimidine and forming an adduct with the 2-hydrocarbyl-3,3-bis(hydroxyaryl)phthalimidine. Then the mixture is heated at a temperature and for a time effective to decompose the adduct and form a 2-hydrocarbyl-3,3-bis(hydroxyaryl)phthalimidine product having a mean particle size greater than 5 microns. The 2-hydrocarbyl-3,3-bis(hydroxyaryl)phthalimidines with increased particle size are useful for producing polymers.

24 Claims, 2 Drawing Sheets

METHODS FOR INCREASING THE MEAN PARTICLE SIZE OF 2-HYDROCARBYL-3,3-BIS(HYDROXYARYL)PHTHALIMIDINES

BACKGROUND

This disclosure relates generally to methods for increasing the mean particle size of a 2-hydrocarbyl-3,3-bis(hydroxyaryl)phthalimidine.

The compounds 2-hydrocarbyl-3,3-bis(hydroxyaryl)phthalimidine (hereinafter abbreviated as "HHP") can be used as monomers for producing polymers such as polycarbonates, which are used in high temperature applications. The HHPs are generally prepared by the reaction of a hydrocarbyl amine compound with a phenolphthalein compound in the presence of an acid catalyst, which is then isolated. The isolated product is usually in the form of a fine powder having a mean particle size of less than 2 microns.

The small particle size (i.e., average particles size less than 2 microns) can cause problems during the preparation of polymers and/or copolymers from the HHPs. Among these problems is that these small particles generate airborne dust, which can cause environmental, health and safety issues, such as the risk of dust explosion in an area where the HHP is stored or handled, such as in a chemical plant environment. Another problem is that the fine nature of the particles causes a "slug flow" behavior during operations such as charging the HHP powder into a polymerization reactor, which in turn may lead to an erratic reaction, or to a reaction that is difficult to control. Further, the "slug flow" behavior also causes problems during general transfer of the fine powder from one container to another, particularly on a large scale, such as in a plant environment.

Therefore, there is a need for methods that produce HHP at an average particles size greater than 5 microns. Furthermore, it would be desirable to develop methods whereby the tap density of the HHP can be increased in addition to increasing the mean particle size.

BRIEF SUMMARY

In one embodiment, a method for increasing a mean particle size of a 2-hydrocarbyl-3,3-bis(hydroxyaryl)phthalimidine is provided. The method comprises forming a mixture of a 2-hydrocarbyl-3,3-bis(hydroxyaryl)phthalimidine having a mean particle size less than 2 microns and a solvent composition comprising an organic solvent and water, wherein the organic solvent is capable of at least partially dissolving the 2-hydrocarbyl-3,3-bis(hydroxyaryl)phthalimidine and forming an adduct with the 2-hydrocarbyl-3,3-bis(hydroxyaryl)phthalimidine. Then the mixture is heated at a temperature and for a time effective to decompose the adduct to form a 2-hydrocarbyl-3,3-bis(hydroxyaryl)phthalimidine product having a mean particle size greater than 5 microns.

In another embodiment, a method for increasing a mean particle size of a 2-hydrocarbyl-3,3-bis(hydroxyaryl)phthalimidine compound comprises contacting the 2-hydrocarbyl-3,3-bis(hydroxyaryl)phthalimidine compound having a mean particle size less than 2 microns with a first solvent composition comprising an organic solvent, wherein the solvent composition is capable of at least partly dissolving the 2-hydrocarbyl-3,3-bis(hydroxyaryl)phthalimidine to form a mixture comprising an adduct of 2-hydrocarbyl-3,3-bis(hydroxyaryl)phthalimidine. Then the mixture is contacted with a second solvent comprising water at a temperature and for a time effective to form a 2-hydrocarbyl-3,3-bis(hydroxyaryl)phthalimidine product having a mean particle size of greater than 5 microns.

In still another embodiment, a method for preparing a 2-hydrocarbyl-3,3-bis(hydroxyaryl)phthalimidine having a mean particle size greater than 5 microns is provided. The method comprises reacting a phenolphthalein compound with a primary hydrocarbyl amine compound, and an acid catalyst to form a 2-hydrocarbyl-3,3-bis(hydroxyaryl)phthalimidine compound. Then a mixture comprising the 2-hydrocarbyl-3,3-bis(hydroxyaryl)phthalimidine compound and a solvent composition comprising at least one organic solvent and water is formed, followed by forming an adduct of the 2-hydrocarbyl-3,3-bis(hydroxyaryl)phthalimidine compound. Then the mixture is heated at a temperature and for a time sufficient to decompose the adduct and form a 2-hydrocarbyl-3,3-bis(hydroxyaryl)phthalimidine product having a mean particle size of greater than 5 microns, wherein the 2-hydrocarbyl-3,3-bis(hydroxyaryl)phthalimidine has a formula:

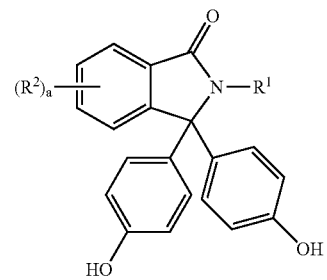

wherein $R^1$ is selected from the group consisting of a hydrogen and a hydrocarbyl group, $R^2$ is selected from the group consisting of a hydrocarbyl group and a halogen; and "a" is 0-4.

In still yet another embodiment, a method of making a polycarbonate is provided. The method comprises reacting a dihydroxy aromatic compound mixture comprising a 2-hydrocarbyl-3,3-bis(hydroxyaryl)phthalimidine with a carbonic acid derivative, wherein the 2-hydrocarbyl-3,3-bis(hydroxyaryl)phthalimidine has a mean particle size of at least about 5 microns.

The disclosure may be understood more readily by reference to the following detailed description of the various features of the disclosure and the examples included therein.

BRIEF DESCRIPTION OF FIGURES

The present disclosure may be understood more readily by reference to the following Figures, wherein.

DETAILED DESCRIPTION

Figure 1:
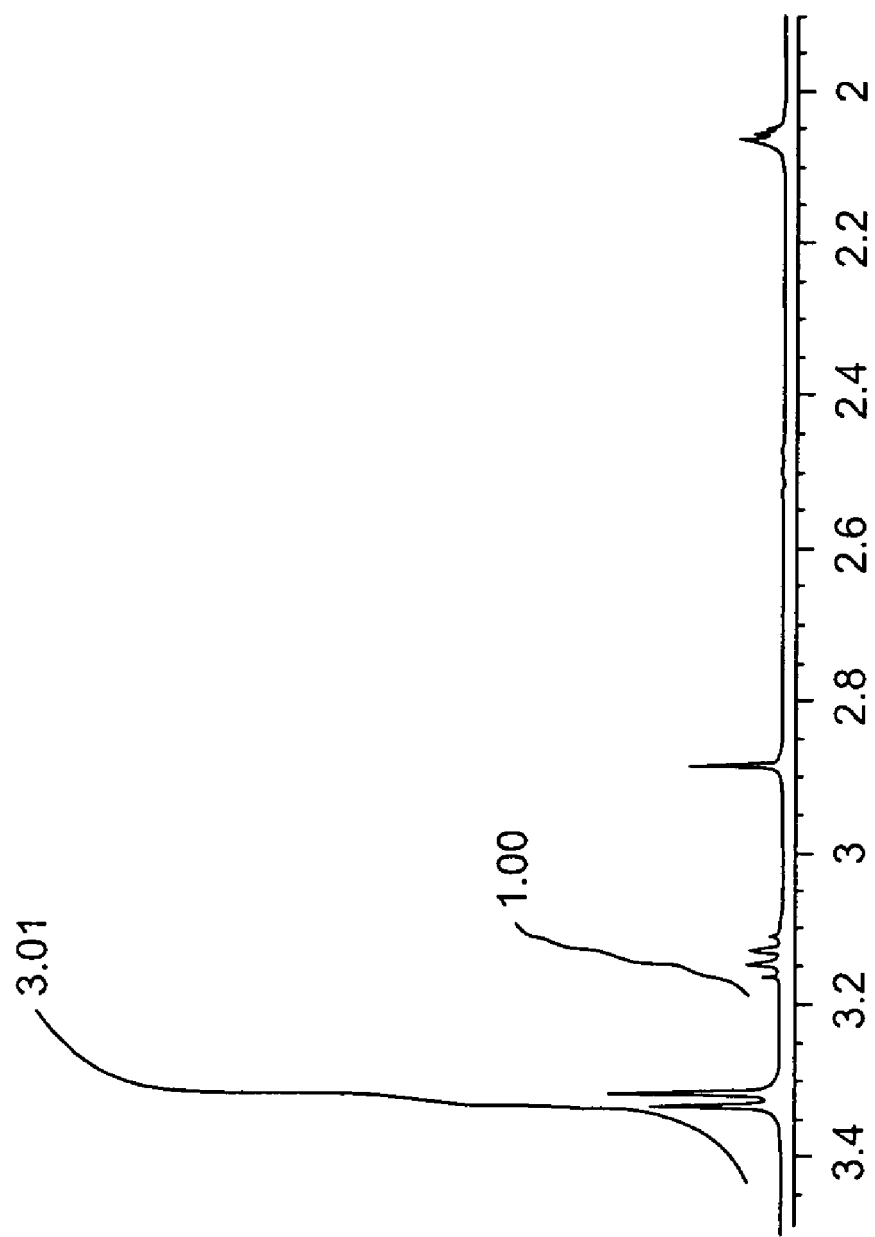
FIG. 1 shows the aliphatic region (2-3.6 parts per million chemical shift scale) of a proton nuclear magnetic resonance spectrum of a solution containing a 2-phenyl-3,3-bis(4-hydroxyphenyl)phthalimidine—methanol adduct in $d_6$—acetone.
Figure 2:
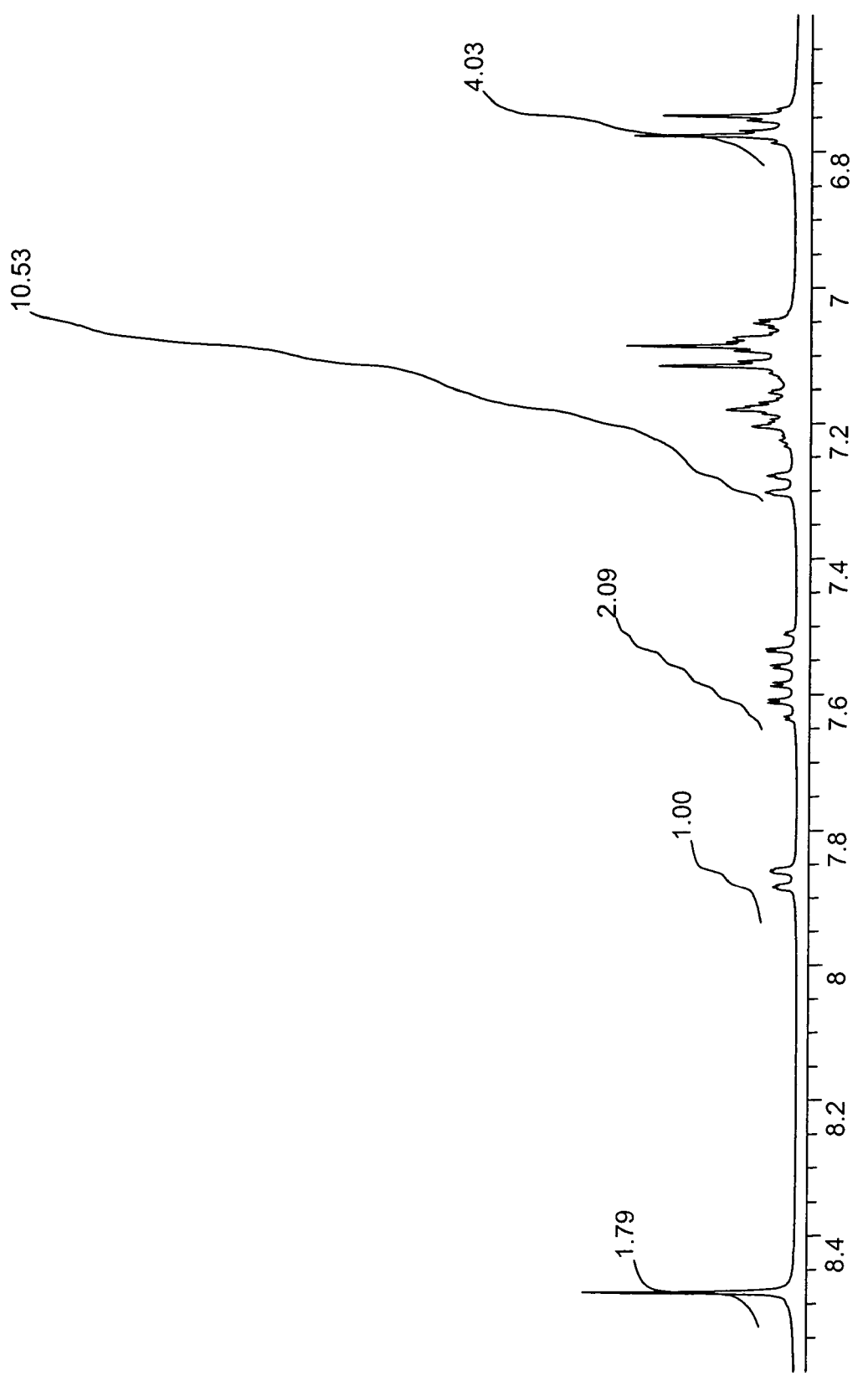
FIG. 2 shows the aromatic region (6.6-8.6 parts per million chemical shift scale) of a proton nuclear magnetic resonance spectrum of the solution of FIG. 1.

In the following description and claims that follow, reference will be made to a number of terms which shall be defined to have the following meanings: the singular forms "a", "an" and "the" include plural referents unless the context clearly dictates otherwise. "Optional" or "optionally" means that the subsequently described event or circumstance may or may not occur, and that the description includes instances where the event occurs and instances where it does not. The term "hydrocarbyl radical" refers to an aliphatic radical, an aromatic or an aryl radical, or a cycloaliphatic radical. The terms "formula" and "structure" are used interchangeably herein.

As disclosed herein, in the structures/formulae for the HHPs or the phenolphthalein compounds, when the subscript "a" in "$(R^2)_a$" is zero, it denotes a structure where all the $R^2$ substituents are hydrogen atoms. In the case where $R^2$ is other than a hydrogen atom, the subscript "a" can take values from zero to four, with a value of zero for "a" denoting a structure having only hydrogen atoms as the $R^2$ substituents.

The term "aliphatic radical" refers to an organic radical having a valence of at least one comprising a linear or branched array of atoms which is not cyclic. The aliphatic radicals comprise at least one carbon atom. The array of atoms forming the aliphatic radical may further include heteroatoms such as nitrogen, sulfur, silicon, selenium and oxygen or may be composed exclusively of carbon and hydrogen. The "linear or branched array of atoms which is not cyclic" is intended to include a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, a suitable aliphatic radical is the 4-methylpent-1-yl radical, which is a $C_6$ aliphatic radical comprising a methyl group. Similarly, the 4-nitrobut-1-yl group is a $C_4$ aliphatic radical comprising a nitro functional group. Other suitable aliphatic radicals include a haloalkyl group that comprises one or more halogen atoms which may be the same or different. Suitable halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl; difluorovinylidene; trichloromethyl, bromodichloromethyl, bromoethyl, 2-bromotrimethylene (e.g. —$CH_2CHBrCH_2$—), and the like. Further examples of suitable aliphatic radicals include allyl, aminocarbonyl (—$CONH_2$), carbonyl, dicyanoisopropylidene (—$CH_2C(CN)_2CH_2$—), methyl (—$CH_3$), methylene (—$CH_2$—), ethyl, ethylene, formyl (—CHO), hexyl, hexamethylene, hydroxymethyl (—$CH_2OH$), mercaptomethyl (—$CH_2SH$), methylthio (—$SCH_3$), methylthiomethyl (—$CH_2SCH_3$), methoxy, methoxycarbonyl ($CH_3OCO$—), nitromethyl (—$CH_2NO_2$), thiocarbonyl, trimethylsilyl (($CH_3)_3Si$—), t-butyldimethylsilyl, trimethyoxysilylpropyl (($CH_3O)_3SiCH_2CH_2CH_2$—), vinyl, vinylidene, and the like. By way of further example, a $C_1$-$C_{10}$ aliphatic radical contains at least one but no more than 10 carbon atoms.

The term "aromatic radical" is also sometimes referred herein to as an "aryl radical". The aromatic radical or the aryl radical refers to an array of atoms having a valence of at least one comprising at least one aromatic group. The aromatic radical may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthraceneyl groups (n=3) and the like. The aromatic radical may also include non-aromatic components. For example, a benzyl group is an aromatic radical that comprises a phenyl ring (the aromatic group) and a methylene group (the non-aromatic component). Similarly a tetrahydronaphthyl radical is an aromatic radical comprising an aromatic group ($C_6H_3$) fused to a non-aromatic component —($CH_2)_4$—. The "aromatic radical" can encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl alkyl group. Similarly, the 2-nitrophenyl group is a $C_6$ aromatic radical comprising a nitro functional group. Suitable aromatic radicals may include halogenated aromatic radicals such as trifluoromethylphenyl, hexafluoroisopropylidenebis(4-phen-1-yloxy)(—$OPhC(CF_3)_2PhO$—), chloromethylphenyl; 3-trifluorovinyl-2-thienyl; 3-trichloromethylphen-1-yl (3-$CCl_3$Ph-), 4(3-bromoprop-1-yl)phen-1-yl ($BrCH_2CH_2CH_2$Ph-), and the like. Further examples of aromatic radicals include 4-allyloxyphen-1-oxy, 4-aminophen-1-yl ($H_2$NPh-), 3-aminocarbonylphen-1-yl ($NH_2$COPh-), 4-benzoylphen-1-yl, dicyanoisopropylidenebis(4-phen-1-yloxy) (—$OPhC(CN)_2PhO$—), 3-methylphen-1-yl, methylenebis(phen-4-yloxy)(—$OPhCH_2PhO$—), 2-ethylphen-1-yl, phenylethenyl, 3-formyl-2-thienyl, 2-hexyl-5-furanyl; hexamethylene-1,6-bis(phen-4-yloxy)(—$OPh(CH_2)_6PhO$—); 4-hydroxymethylphen-1-yl (4-$HOCH_2$Ph-), 4-mercaptomethylphen-1-yl (4-$HSCH_2$Ph-), 4-methylthiophen-1-yl (4-$CH_3$SPh-), 3-methoxyphen-1-yl, 2-methoxycarbonylphen-1-yloxy (methyl salicyl), 2-nitromethylphen-1-yl (—$PhCH_2NO_2$), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_8$—) represents a $C_7$ aromatic radical.

The term "cycloaliphatic radical" refers to a radical having a valence of at least one and comprising an array of atoms that is cyclic but not aromatic. As defined herein a "cycloaliphatic radical" does not contain an aromatic group and may further include one or more noncyclic components. For example, a cyclohexylmethyl group ($C_6H_{11}CH_2$—) is a cycloaliphatic radical that comprises a cyclohexyl ring (the array of atoms is cyclic but not aromatic) and a methylene group (the noncyclic component). The cycloaliphatic radical may further include heteroatoms such as nitrogen, sulfur, selenium, silicon and oxygen, or may be composed exclusively of carbon and hydrogen. In addition, the cycloaliphatic radical can encompass a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A suitable cycloaliphatic radical may also comprise one or more halogen atoms which may be the same or different. Suitable halogen atoms include, for example; fluorine, chlorine, bromine, and iodine. Suitable cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene2,2-bis(cyclohex-4-yl) (—$C_6H_{10}C(CF_3)_2C_6H_{10}$—), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}$—), and the like. Further examples of cycloaliphatic radicals include 4-allyloxycyclohex-1-yl, 4-aminocyclohex-1-yl ($H_2NC_6H_{10}$—), 4-aminocarbonylcyclopent-1-yl ($NH_2COC_5H_8$—), 4-acetyloxycyclohex-1-yl, 2,2-dicyanoisopropylidenebis(cyclohex-4-yloxy)(—$OC_6H_{10}C(CN)_2C_6H_{10}O$—), 3-methylcyclohex-1-yl, methylenebis(cyclohex-4-yloxy) (—$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl; hexamethylene-1,6-bis(cyclohex-4-yloxy) (—$OC_6H_{10}(CH_2)_6C_6H_{10}O$—); 4-hydroxymethylcyclohex-1-yl (4-$HOCH_2C_6H_{10}$—), 4-mercaptomethylcyclohex-1-yl (4-$HSCH_2C_6H_{10}$—), 4-methylthiocyclohex-1-yl (4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl ($NO_2CH_2C_6H_{10}$—), 3-trimethylsilylcyclohex-1-yl, 2-t-butyidimethylsilylcyclopent-1-yl, 4-trimethoxysilylethylcyclohex-1-yl (($CH_3O)_3SiCH_2CH_2C_6H_{10}$—), 4-vinylcyclohexen-1-yl, vinylidenebis (cyclohexyl), and the like.

As disclosed herein, the mean particle size is defined as the average of the size of all particles present in a given sample. The size of all particles present in any sample can be characterized by a particle size distribution (PSD). The PSD depends upon many factors, including the nature of the feed sample, and the method used for the particle size enhancement. The PSD may be mono-modal, bi-modal, or multi-modal. The mean particle size is expressed in microns, and is measured using a particle size analyzer, which determines both the size of particles and their state of distribution. For a given mean particle size, the state of the particle size distribution is given by a median particle size, a mode particle size, and a particle size range. The particle size range can be given as a range from the size of the smallest particle to the size of the largest particle. The particle size range can also be given by the difference between the highest and the lowest measured particle size values. For example, the mean particle size of a sample of 2-phenyl-3,3-bis(4-hydroxyphenyl)phthalimidine (abbreviated as "PPPBP") as measured with the particle size analyzer is 1.7 microns, and the state of the particle size distribution is given by a median particle size of 1.6 microns, a mode of 1.8 microns, and a particle size range of 0.3 microns to 4 microns, or 3.7 microns.

As mentioned previously, the present disclosure provides a method for increasing a mean particle size of a 2-hydrocarbyl-3,3-bis(4-hydroxyaryl)phthalimidine isolated compound to an average particle size greater than 5 microns. The so-called particle size enhancement process can be carried out either before or after the isolated product (having a an average particles size less than 2 microns) has been purified to remove phenolphthalein and other impurities. The method comprises forming a mixture of the isolated 2-hydrocarbyl-3,3-bis(4-hydroxyaryl)phthalimidine (having a mean particle size less than 2 microns) and a solvent composition comprising an organic solvent and water, wherein the organic solvent is capable of at least partially dissolving the HHP and forming an adduct with the HHP. The mixture is then heated at a temperature and for a time effective to decompose the adduct, and form a HHP product having a mean particle size greater than 5 microns.

The HHP has the general formula (I):

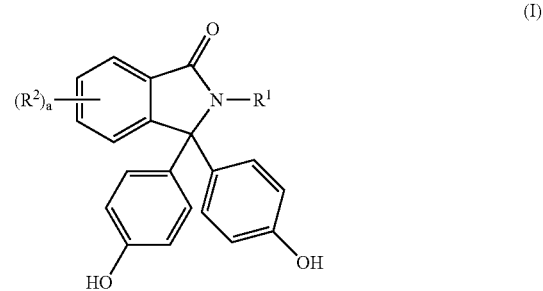

wherein $R^1$ is selected from the group consisting of a hydrogen and a hydrocarbyl group, $R^2$ is selected from the group consisting of a hydrocarbyl group and a halogen; and "a" is 0-4. To clarify, when "a" is less than 4, each unsubstituted carbon on the aryl ring is bonded to a hydrogen atom, as is the accepted chemical shorthand. Further structures presented below are similar.

As previously discussed, the isolated 2-hydrocarbyl-3,3-bis(4-hydroxyaryl)phthalimidine product (having a mean particle size less than 2 microns) can be obtained from the reaction of a phenolphthalein compound with a hydrocarbyl amine compound in the presence of an acid catalyst. In another embodiment, the isolated 2-hydrocarbyl-3,3-bis(4-hydroxyaryl)phthalimidine product is obtained by subjecting the reaction product to a base treatment step, followed by treatment with a decolorizing agent, as will be discussed in greater detail below.

The phenolphthalein compound has a formula (II):

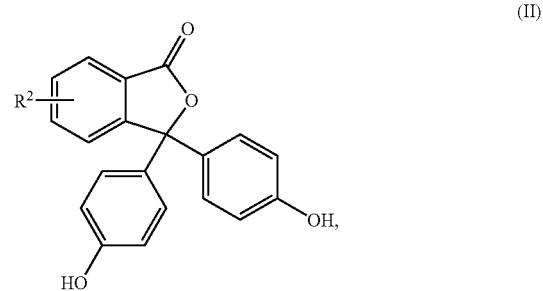

wherein $R^2$ is as previously described.

The hydrocarbyl amine compound has a formula (III):

 

wherein R³ is a hydrocarbyl radical. Suitable hydrocarbyl amines include the aromatic amines of the formula (IV):

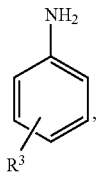

(IV)

wherein R³ is as defined above. Examples of suitable aromatic amines include, but are not limited to aniline ($C_6H_5NH_2$), anilines substituted by one or more $C_1$-$C_{12}$ aliphatic radicals, one or more $C_3$-$C_{12}$ cycloaliphatic radicals, or one or more aromatic radicals.

The acid catalyst facilitates the condensation of the hydrocarbyl amine compound with the phenolphthalein compound. Suitable acid catalysts that can be used for forming the 2-hydrocarbyl-3,3-bis(4-hydroxyaryl)phthalimidines include amine salts of mineral acids. Examples of suitable mineral acids include hydrochloric acid, sulfuric acid, and the like. Examples of suitable amines include primary, secondary, and tertiary amines having any combination of aliphatic and aromatic groups bonded to the amine nitrogen. Suitable examples of amine salt catalysts include primary, secondary, and tertiary amine hydrochlorides. Hydrochloride salts of the primary aromatic amines, which also serve as the starting material for preparing the HHP compounds, are preferred. For example, aniline hydrochloride can be used as the catalyst in the reaction of phenolphthalein (wherein R² in formula (II) is hydrogen) with aniline for preparing the HHP of formula (I), wherein R¹ is a phenyl radical, and R² is hydrogen.

In one embodiment, the catalyst is introduced as a preformed salt into the reactor. In another embodiment, the catalyst is generated in the reactor by first charging the hydrocarbyl amine compound of formula (III) or (IV) into the reactor, and then adding about ⅓ to about 1 part by weight of an appropriate mineral acid to the phenolphthalein compound of formula (II). In still another embodiment, about 0.1 parts to about 0.3 parts by weight of hydrogen chloride gas is introduced into a reactor charged with the hydrocarbyl amine compound to form an appropriate amount of the amine hydrochloride catalyst. More hydrochloric acid or more hydrogen chloride gas can also used, but is generally not required. A solvent can optionally be employed to form the hydrocarbyl amine hydrochloride. The solvent can then be removed (if necessary), and the amine can be added, followed by addition of phenolphthalein compound of formula (II).

An excess of the hydrocarbyl amine compound over the phenolphthalein compound may be used to keep the reaction proceeding in the forward direction. The condensation reaction proceeds with formation of water as a by-product. A higher reaction temperature with or without removal of water by-product also facilitates product formation.

The reaction mixture thus obtained is quenched with an aqueous mineral acid, such as aqueous hydrochloric acid, and the crude product is precipitated from the solution. The precipitate is in the form of a powder having a mean particle size less than 2 microns. The isolated product can then be dissolved in an aqueous inorganic base, such as an alkali metal or alkaline earth metal hydroxide, carbonate, or bicarbonate. Then, the resulting solution can be treated with a suitable solid adsorbent, such as for example, activated carbon. Suitable activated carbon materials include the NORIT series of activated carbons available commercially from Norit Corporation, and those activated carbons commercially available from E. Merck Company. The activated carbon functions, inter alia, as a decolorization agent. After treatment with the activated carbon, the resulting mixture is filtered to provide a decolorized solution.

The decolorized solution is next treated with an aqueous mineral acid, such as aqueous hydrochloric acid to precipitate the HHP. The precipitate is then stirred with an aliphatic alcohol to remove any trace of the phenolphthalein compound that may still be present, and subsequently filtered to provide the isolated 2-hydrocarbyl-3,3-bis(4-hydroxyaryl) phthalimidine product having a mean particle size less than 2 microns.

Suitable aliphatic alcohols include any aliphatic monohydric or dihydric alcohol. Non-limiting examples of suitable aliphatic alcohols include methanol, ethanol, iso-propanol, iso-butanol, n-butanol, tertiary butanol, n-pentanol, iso-pentanol, cyclohexanol, ethylene glycol, propylene glycol, neopentyl glycol and the like. In a particular embodiment, aliphatic monohydric alcohols that are miscible with water, such as methanol, ethanol, and isopropanol are used. Methanol is an exemplary aliphatic alcohol for removing phenolphthalein.

In one embodiment, the isolated 2-hydrocarbyl-3,3-bis(4-hydroxyaryl)phthalimidine having the mean particle size les than 2 microns is contacted with a solvent composition comprising water and an organic solvent. The organic solvent is capable of at least partly dissolving the 2-hydrocarbyl-3,3-bis(4-hydroxyaryl)phthalimidine, which forms an adduct of the 2-hydrocarbyl-3,3-bis(4-hydroxyaryl)phthalimidine and the organic solvent. Generally, organic solvents that are capable of at least partly dissolving the 2-hydrocarbyl-3,3-bis(4-hydroxyaryl)phthalimidine are also capable of forming the adduct. Depending upon the nature of the organic solvent, the kinetics of adduct formation can vary. Thus, in one embodiment, if the solvent composition is capable of fully dissolving the 2-hydrocarbyl-3,3-bis(4-hydroxyaryl)phthalimidine, all or a part of the 2-hydrocarbyl-3,3-bis(4-hydroxyaryl)phthalimidine may form the adduct with the solvent composition. In another embodiment, if the organic solvent is capable of only partly dissolving the 2-hydrocarbyl-3,3-bis(4-hydroxyaryl)phthalimidine in the feedstream, the resulting mixture may comprise some of the adduct with the remaining 2-hydrocarbyl-3,3-bis(4-hydroxyaryl)phthalimidine remaining in a free form (that is, it does not exist in the adduct form).

As discussed above, the solvent composition comprises water and an organic solvent. Generally, the isolated 2-hydrocarbyl-3,3-bis(4-hydroxyaryl)phthalimidine compounds are insoluble in water. Without wishing to be bound by any theory, it is believed that that the organic solvent is capable of forming hydrogen bonds with the 2-hydrocarbyl-3,3-bis(4-hydroxyaryl)phthalimidine compound and is able to at least partly dissolve the 2-hydrocarbyl-3,3-bis(4-hydroxyaryl)phthalimidine. Formation of hydrogen bonds can occur with the one or both phenolic OH groups, or with the carbonyl group, or the amide nitrogen, or combinations thereof, present in the 2-hydrocarbyl-3,3-bis(4-hydroxyaryl) phthalimidine compound of Formula (I).

Suitable organic solvents useful for increasing the mean particle size of the HPP are those solvents at least partly miscible with water. In other embodiments, suitable organic solvents are those solvents fully miscible with water. Suitable organic solvents comprise at least one functional group selected from the group consisting of a hydroxy group, a ketone carbonyl group, a carboxylic acid group, an ester group, a sulfoxide group, a nitrile group, a nitro group, and an amine group. In an embodiment, suitable organic solvents are selected from the group consisting of an organic hydroxy compound, an organic ketone compound, an organic amide compound, an organic sulfoxide compound, an organic nitrile compound, and an organic amine compound. Each of these categories of solvents may comprise more than one functional group, which may be the same or different from the other functional group(s). For example ethanol, ethylene glycol, and 2-aminoethanol may be used, either individually, or in any relative proportion as suitable organic solvents.

Suitable organic hydroxy compounds that are at least partly miscible with water include aliphatic, cycloaliphatic and aromatic hydroxy compounds having at least one hydroxy group. The aliphatic hydroxy compounds include linear and branched aliphatic mono-hydroxy compounds, non-limiting examples of which are methanol, ethanol, isopropanol, n-butanol, sec-butanol, iso-butanol, tert-butanol, and the like. Mixtures of these compounds can also be used. Aliphatic dihydroxy compounds, such as the glycols, exemplified by ethylene glycol, propylene glycol, and the like may also be used. Non-limiting examples of aromatic hydroxy compounds include phenol, ortho-cresol, benzyl alcohol, and the like. Some examples of cycloaliphatic hydroxy compounds include cyclopentanol, cyclohexanol, cyclohexanediol, and the like. In an embodiment, suitable organic hydroxy compounds include methanol, isopropanol, or any combination of methanol and isopropanol.

Organic ketones suitable for use as the organic solvent include acetone, 2-butanone, methyl ethyl ketone, diethyl ketone, methyl isopropyl ketone, and the like. In an embodiment, the organic solvent comprises acetone. Suitable organic amides include formamide, acetamide, and the like. Organic sulfoxides that may be used as the organic solvent include dimethyl sulfoxide, methyl ethyl sulfoxide, diethyl sulfoxide, and the like. Non-limiting examples of organic nitrites include the aliphatic nitrites, such as acetonitrile, propionitrile, butyronitrile, hexanedinitrile, and the like. Non-limiting examples of organic amines include the aliphatic amines, such as methyl amine, ethyl amine, propyl amine, butyl amine, 1,2-diaminoethane, 1,3-propanediamine, 1,4-butanediamine, and the like; and aromatic amines, such as for example aniline, methoxanilines, toluidines, and the like. Cycloaliphatic amines are exemplified by cyclohexylamine and related compounds. Examples of organic nitro compounds that may be used include nitromethane, nitroethane, and the like. In an embodiment, the organic solvent is methanol, ethanol, isopropanol, sec-butanol, phenol, acetone, butanone, formamide, methyl amine, isopropyl amine, dimethylsulfoxide, aniline, or a combination of the foregoing compounds. As pointed out previously, organic solvents that have any combination of the functional groups, illustrated above with some examples, may be used so long as they are at least partly miscible with water.

The nature of the adduct and the relative stoichiometry of the 2-hydrocarbyl-3,3-bis(4-hydroxyaryl)phthalimidine compound and the organic solvent molecules constituting the adduct varies depending upon the structure of the 2-hydrocarbyl-3,3-bis(4-hydroxyaryl)phthalimidine and the structure and nature of the organic solvent. In the case of 2-phenyl-3,3-bis(4-hydroxyphenyl)phthalimidine (PPPBP), the adducts have a molar ratio of 1:x of the PPPBP and the organic solvent, respectively; wherein "x" has a value of from about 0.5 to 2. The organic solvent can be any of the solvents described previously herein. In an embodiment, the organic solvent that can form an adduct is selected from the group consisting of methanol, ethanol, isopropanol, sec-butanol, phenol, acetone, butanone, formamide, methyl amine, isopropyl amine, formamide, dimethylsulfoxide, and aniline. For example, methanol and PPPBP form an adduct having the formula 1 PPPBP:1 $CH_3OH$. On the other hand, acetone forms an adduct with PPPBP having the formula 1 PPPBP:0.5 acetone. The organic solvent in these adducts is tightly bound to the PPPBP molecule as seen from the fact that these materials have relatively high decomposition temperatures. For example, the 1 PPPBP:1 $CH_3OH$ adduct decomposes at a temperature of about 150° C. at ambient pressure.

Another example is the adduct with isopropanol (hereinafter abbreviated as "IPA") having the approximate formula 2 PPPBP:1 $(CH_3)_2CHOH$ adduct, which decomposes at a temperature of about 170° C. at ambient pressure as measured by thermogravimetric analysis or differential scanning calorimetry. The loss of the solvent molecule from the adduct, and the amount of solvent present in the adduct can be monitored by a known technique, such as headspace gas chromatography. Furthermore, the adducts can be characterized by nuclear magnetic resonance spectroscopy. For example, the proton nuclear magnetic resonance spectrum of the 1:1 methanol:PPPBP adduct in $d_6$—acetone is shown in FIG. 1, which clearly shows the phenolic OH protons of the PPPBP molecule split into a characteristic quartet (having a 1:3:3:1 relative peak intensity) which indicates the splitting by the three protons of the methanol molecule. The adducts of organic solvents with HHPs, such as PPPBP may be useful materials for other purposes, for example, carrying out further downstream processing, other synthetic reactions, and polymerization reactions. They may also aid in stabilizing the HHPs from atmospheric degradation and thus preserve their quality.

Regardless of the physical nature of the combination of the HHP and the solvent mixture, the mixture is then heated at a temperature and for a time effective to decompose the adduct and form a 2-hydrocarbyl-3,3-bis(4-hydroxyaryl) phthalimidine having an increased particle size greater than 5 microns. Without wishing to be bound by any theory, it is believed that upon the application of heat, the adduct in the mixture decomposes to form "nascent" particles of 2-hydrocarbyl-3,3-bis(4-hydroxyaryl)phthalimidine, which under the prevailing conditions are capable of coalescing into particles having a larger average size. It is also believed that water aids in the decomposition of the adduct and formation of the "nascent" particles. Furthermore, it is also believed that the mean particle size depends upon the time for which the heating step is carried out. A longer heating time generally results in particles having a relatively greater average particle size. The time can range from about 0.5 hour to about 10 hours in an embodiment, and from about 1 hour to about 4 hours in another embodiment. The temperature can range from about 40° C. to about the boiling point of the mixture in an embodiment, and from about 50° C. to about 100° C. in another embodiment. For example, with methanol as the organic solvent, a temperature in the range from about 40° C. to about 80° C. can be used. Thus, the method described hereinabove can be used for producing HHPs greater than about 5 microns in an embodiment, and up to about 250 microns in another embodiment.

Generally, for any of the particle size enhancement methods disclosed herein, the process can be further expedited by using small amounts of an acidic material. For example, liquid acidic materials, such as liquid inorganic and organic acids can be used. Some examples of liquid acidic materials include hydrochloric acid, sulfuric acid, phosphoric acid, formic acid, trifluoroacetic acid, acetic acid, and the like. Solid acidic materials like benzoic acid may also be used. The amount of acid to be used can be in a range from about 0.01 weight percent to about 10 weight percent, based on the combined weight of the water and organic solvent(s) employed.

In some instances, there may be a need to recycle some part of the HHP—organic solvent adduct to the process vessel where the particle size enhancement is to be conducted. In such cases, the recycled HHP may further comprise the adduct, which can then be isolated as HHP having a particle size greater than 5 microns.

In accordance with another embodiment of the present disclosure, the increase in average particle size of the HHPs to greater than 5 microns can be achieved by a process comprising two solvent treatment steps. First, the HHP having a mean particle size less than 2 microns is contacted with a first solvent comprising a organic solvent that is capable of at least partly dissolving the HHP to form a mixture comprising an adduct of 2-hydrocarbyl-3,3-bis(hydroxyaryl)phthalimidine and the organic solvent. Then the mixture is contacted with a second solvent comprising water at a temperature and for a time effective to form a HHP product having a mean particle size of greater than 5 microns. In this method, the first solvent does not comprise water, but is miscible with water, and is capable of at least partly dissolving the HHP. But the second solvent comprises water to aid in the decomposition of the adduct and formation of bigger particles of HHP having a mean particle size greater than 5 microns. The second solvent may further comprise an organic solvent that is at least partly miscible with water. Non-limiting examples of such organic solvents that may be present in the second solvent include those selected from the group consisting of water-soluble aliphatic alcohols, aliphatic amines, aliphatic ketones, aliphatic amides, and aliphatic nitrites. Thus, the organic solvent present in the first solvent and the organic solvent present in the second solvent comprising water can be the same in an embodiment, and in another embodiment, they can be different. The various types of organic solvents that can be used in this method have already been described in this disclosure. In an embodiment, the method can be used for producing HHPs and PPPBP having a mean particle size greater than about 5 microns to about 100 microns.

In an embodiment, the process for enhancing the mean particle size of HHPs can also aid in purification of the HHPs by removing any impurities, especially residual phenolphthalein that may be present as an impurity. For example, in the case of PPPBP, it is believed that residual phenolphthalein that can get trapped within the adduct is released during the decomposition of the adduct (described previously) thereby leading to a purer form of PPPBP. The amount of phenolphthalein present in the HHPs is less than about 1000 parts per million in an embodiment, and less than about 500 parts per million in another embodiment.

The methods described in this disclosure for enhancing the particle size of HHPs in general, and PPPBP in particular, can be coupled with a process for making the HHPs or the PPPBP by the condensation reaction (also described previously herein). In an embodiment, particle size enhancement can also be achieved during the process of isolating the HHP from the reaction mixture. After the formation of the HHP in the reaction mixture is complete, excess aromatic amine of formula (IV) is removed by distillation techniques, such as azeotropic distillation. Steam distillation may also be used. Water is used to remove the aromatic amine as an azeotrope. Other solvents that can form an azeotrope with the aromatic amine can also be used. Generally, it has been observed that during the azeotropic distillation, HHP or PPPBP particles having an enhanced mean particle size are produced. Therefore, HHPs like PPPBP, having an enhanced mean particle size can be produced directly from the azeotropic distillation set-up. The product isolated in this manner may be sufficiently pure for further use, such as for making other monomers or derivatives, or as a monomer for producing polymers, such as polycarbonates.

The PPPBP sample having an enhanced mean particle size also has better flow characteristics, as measured by the so-called "angle of repose". The angle of repose is an engineering property of particulate solids. When bulk particles are poured onto a horizontal surface, a conical pile will form. The angle between the edge of the pile and the horizontal surface is known as the angle of repose, and is related to the density, surface area, and coefficient of friction of the material. The angle of repose partially reflects the flow behavior of particles. This property is sometimes used in the design of equipment for the processing of particulate solids. For example, it may be used to design an appropriate hopper or silo to store the material. It can also be used to size a conveyor belt for transporting the material. A material with a lower angle of repose forms flatter piles than a material with a higher angle of repose. Typically, the higher the angle of repose, the higher is the inter-particle, resistance and hence the poorer the flow characteristics of the particles. For example, it is known that the angle of repose of a heavy sodium carbonate (having a comparatively higher tap density relative to a light sodium carbonate) sample is about 31°, whereas it is about 41° for a light sodium carbonate. Talc generally has a higher angle of repose. For example, the following materials have the angle of repose in a decreasing order: talc>light sodium carbonate>heavy sodium carbonate. Sand generally has the lowest angle of repose, or in other words, has the best flow characteristics. The angle of repose is one of many parameters that affect flow properties of powders, such as for example, un-confined yield strength, yield loci for different bed heights in a bin, minimum fluidization velocity, moisture content, and the ability to pick up electrostatic charge.

The HHPs and PPPBP having an increased particle size greater than 5 microns can be used safely and advantageously as a monomer or as a comonomer for producing polymers, polymer blends, and copolymers; such as polycarbonate homopolymers, polymer blends, or copolymers. To make the polycarbonate copolymers, a carbonic acid derivative, at least one aromatic dihydroxy compound and a HHP, such as PPPBP is used. Aromatic dihydroxy compounds have the general formula (V), $$HO\text{-}[A]\text{-}OH \qquad (V)$$

wherein [A] is a divalent aromatic radical. The moiety [A] can be represented by a structure (VI),

$$(VI)$$

wherein each $G^1$ is independently at each occurrence a $C_6$-$C_{20}$ aromatic radical; E is independently at each occurrence a bond, a $C_3$-$C_{20}$ cycloaliphatic radical, a $C_3$-$C_{20}$ aromatic radical, a $C_1$-$C_{20}$ aliphatic radical, a nitrogen-containing linkage, a silicon-containing linkage, a sulfur-containing linkage, a selenium-containing linkage, a phosphorus-containing linkage, or an oxygen atom; "t" is a number greater than or equal to one; "s" is either zero or one; and "u" is a whole number including zero. In various embodiments, "t" can have values from 1 to 10, from 1 to 5, from 1 to 3, and preferably 1. Similarly, in various embodiments "u" can have values from 1 to 10, from 1 to 5, from 1 to 3, and specifically 1.

As defined herein, a "nitrogen-containing linkage" includes tertiary nitrogen-containing linkages. As defined herein, a "silicon-containing linkage" includes silane type linkages and siloxane type linkages. As defined herein, a "sulfur-containing linkage" includes a sulfide group, a sulfoxide group, and a sulfone group. As defined herein, a "selenium-containing linkage" includes a selenide group, a selenoxide group, and a selenone group. As defined herein, a "phosphorus-containing linkage" is defined to include trivalent, tetravalent, or pentavalent phosphorus, some non-limiting examples of which include the phosphonyl and phosphinyl type linkages. The phosphorus atom may be bonded through carbon-containing groups, oxygen-containing groups, sulfur-containing groups, or selenium-containing groups. In some embodiments, the phosphorus atom may be bonded to other inorganic groups, such as for example hydroxy groups or their metal salt derivatives, such as ONa, OK, OLi, and the like. The phosphorus atom may also be bonded through oxygen, sulfur, or selenium to organic groups, such as $C_3$-$C_{20}$ cycloaliphatic radicals, $C_3$-$C_{20}$ aromatic radicals, or $C_1$-$C_{20}$ aliphatic radicals.

Some illustrative, non-limiting examples of aromatic dihydroxy compounds include, but are not limited to, 2,4'-dihydroxydiphenylmethane, bis(2-hydroxyphenyl)methane, bis(4-hydroxyphenyl)methane, bis(4-hydroxy-5-nitrophenyl)methane, bis(4-hydroxy-2,6-dimethyl-3-methoxyphenyl)methane, 1,1-bis(4-hydroxyphenyl)ethane, 1,1-bis(4-hydroxy-2-chlorophenyl)ethane, BPA, 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-disopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 2,2-bis(4-hydroxy-3-ethylphenyl)propane, 2,2-bis(4-hydroxy-3,5-dimethylphenyl)propane, 2,2-bis(3,5,3',5'-tetrachloro-4,4'-dihydroxyphenyl)propane, bis(4-hydroxyphenyl)cyclohexylmethane, 2,2-bis(4-hydroxyphenyl)-1-phenylpropane, 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(4'-hydroxy-3'methylphenyl)cyclohexane (DMBPC), 1,1-bis(3,5-dimethyl-4-hydroxyphenyl)cyclohexane; 4,4'-[1-methyl-4-(1-methyl-ethyl)-1,3-cyclohexandiyl]bisphenol (1,3 BHPM), 4-[1-[3-(4-hydroxyphenyl)-4-methylcyclohexyl]-1-methyl-ethyl]-phenol (2,8 BHPM), 3,8-dihydroxy-5a,10b-diphenylcoumarano-2',3',2,3-coumarane (DCBP), 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl-4-hydroxyphenyl)cyclohexane; 1,1-bis(3,5-disopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-disopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4-bis(4-hydroxyphenyl)heptane, 4,4'-(3,3,5-trimethylcyclohexylidene)diphenol, 4,4'-bis(3,5- dimethyl)diphenol, 4,4'-dihydroxydiphenylether; 4,4'-dihydroxydiphenylthioether; 1,3-bis(2-(4-hydroxyphenyl)-2-propyl)benzene; 1,3-bis(2-(4-hydroxy-3-methylphenyl)-2-propyl)benzene; 1,4-bis(2-(4-hydroxyphenyl)-2-propyl)benzene, 1,4-bis(2-(4-hydroxy-3-methylphenyl)-2-propyl)benzene 2,4'-dihydroxyphenylsulfone, 4,4'-dihydroxydiphenylsulfone (BPS), bis(4-hydroxyphenyl)methane, 2,6-dihydroxynaphthalene; resorcinol, $C_1$-$C_3$ alkyl-substituted resorcinols, 3-(4-hydroxyphenyl)-1,1,3-trimethylindan-5-ol, 1-(4-hydroxyphenyl)-1,3,3-trimethylindan-5-ol, 4,4'dihydroxy-1,1-biphenyl (also called 4,4'-biphenol), 3,3'-dichloro-4,4'-dihydroxy-1,1'-biphenyl, 3,3'-difluoro-4,4'-dihydroxy-1,1'-biphenyl 3,3'-bis(trifluoromethyl)-4,4'-dihydroxy-1,1'-biphenyl, and 2,2,2',2'-tetrahydro-3,3,3',3'-tetramethyl-1,1'-spirobi[1H-indene]-6,6'-diol (SBI). In a particular embodiment, the aromatic dihydroxy compound is BPA. In another embodiment, the aromatic dihydroxy compound is selected from the group consisting of BPA, 4,4'-BP, resorcinol, SBI, and DMBPC The carbonic acid derivative described above has the general formula (VII), $$(ZO)_2C=O \tag{VII}$$

wherein each Z is independently an unsubstituted or substituted aryl radical. Suitable examples of carbonic acid derivatives include, but are not intended to be limited to, the carbonyl halides, such as carbonyl chloride (phosgene), and carbonyl bromide; and the carbonic acid diesters (also called diaryl carbonates) such as carbonyl ditolyl carbonate, m-cresyl carbonate, dinaphthyl carbonate, diphenyl carbonate, diethyl carbonate, dimethyl carbonate, dibutyl carbonate, dicyclohexyl carbonate, and combinations of two or more carbonic acid diesters thereof. Carbonyl chloride is used widely in the interfacial polymerization process for producing polycarbonates, and is well known in the art. Diphenyl carbonate is widely used as a carbonic acid diester in melt polymerization processes due to its low cost and ready availability on a commercial scale. If two or more of the carbonic acid diesters listed above are utilized, it is advantageous if one of the carbonic acid diesters is diphenyl carbonate.

Suitable carbonic acid diesters include the group of "activated aromatic carbonates". As used herein, the term "activated aromatic carbonate" is defined as a diaryl carbonate that is more reactive than diphenyl carbonate in a transesterification reaction. Such activated aromatic carbonates can also be represented by formula (VII), wherein each Z is an aryl radical having 6 to 30 carbon atoms. The activated carbonates have the general formula (VIII),

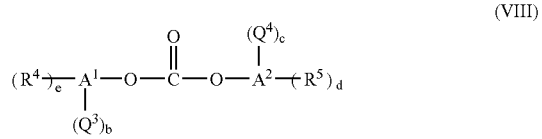

wherein $A^1$ and $A^2$ are each independently aromatic rings each having a number of positions available for substitution; $R^4$ and $R^5$ are independently at each occurrence a halogen, a cyano group, a nitro group, a $C_1$-$C_{20}$ alkyl group, a $C_4$-$C_{20}$ cycloalkyl group, a $C_4$-$C_{20}$ aromatic group, a $C_1$-$C_{20}$ alkoxy group, a $C_4$-$C_{20}$ cycloalkoxy group, a $C_4$-$C_{20}$ aryloxy group, a $C_1$-$C_{20}$ alkylthio group, a $C_4$-$C_{20}$ cycloalkylthio group, a $C_4$-$C_{20}$ arylthio group, a $C_1$-$C_{20}$ alkylsulfinyl group, a $C_4$-$C_{20}$ cycloalkylsulfinyl group, a $C_4$-$C_{20}$ arylsulfinyl group, a $C_1$-$C_{20}$ alkylsulfonyl group, a $C_4$-$C_{20}$ cycloalkylsulfonyl group, a $C_4$-$C_{20}$ arylsulfonyl group, a $C_1$-$C_{20}$ alkoxycarbonyl group, a $C_4$-$C_{20}$ cycloalkoxycarbonyl group, a $C_4$-$C_{20}$ aryloxycarbonyl group, a $C_2$-$C_{60}$ alkylamino group, a $C_6$-$C_{60}$ cycloalkylamino group, a $C_5$-$C_{60}$ arylamino group, a $C_1$-$C_{40}$ alkylaminocarbonyl group, a $C_4$-$C_{40}$ cycloalkylaminocarbonyl group, a $C_4$-$C_{40}$ arylaminocarbonyl group, and a $C_1$-$C_{20}$ acylamino group; "d" and "e" are independently integers from and including 0 to the number of positions available for substitution on $A^1$ and $A^2$ respectively; $Q^3$ and $Q^4$ are each independently activating groups selected from the group consisting of an alkoxycarbonyl group, a formyl group, a halogen atom, a nitro group, an amide group, a sulfone group, a sulfoxide group, an imine group, an amidine group, and aminocarbonyl and amidine moieties having structures (IX) and (X):

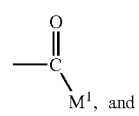 (IX)

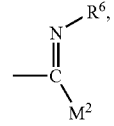 (X)

wherein $M^1$ and $M^2$ are independently N-alkyl, N,N-dialkyl, N-aryl, N,N-diaryl, or N-alkylaryl, N,N-dialkylaryl, and $R^6$ is an alkyl group or an aryl group; and "b" and "c" are independently integers from and including 0 to the number of positions available for substitution on $A^1$ and $A^2$ respectively, provided b+c is greater than or equal to 1. One or more such activated aromatic carbonates may be used for forming the hydroquinone polycarbonate copolymers.

Specific non-limiting examples of activated aromatic carbonates include bis(o-methoxycarbonylphenyl)carbonate, bis(o-chlorophenyl)carbonate, bis(o-nitrophenyl)carbonate, bis(o-acetylphenyl)carbonate, bis(o-phenylketonephenyl)carbonate, bis(o-formylphenyl)carbonate. Unsymmetrical combinations of these structures, wherein the substitution number and type on $A^1$ and $A^2$ are different, can also be used. Examples of activated aromatic carbonates suitable for use include, but are not limited to, bis(methylsalicyl)carbonate (CAS Registry No. 82091-12-1) (also known as BMSC or bis(o-methoxycarbonylphenyl)carbonate), bis(ethyl salicyl) carbonate, bis(propyl salicyl)carbonate, bis(butylsalicyl) carbonate, bis(benzyl salicyl)carbonate, bis(methyl 4-chlorosalicyl)carbonate and the like. In an embodiment, BMSC is used in melt polycarbonate synthesis. Mixtures of DPC and BMSC can also be used.

Unsymmetrical diaryl carbonates, wherein one aryl group is activated and one aryl is inactivated, can be useful if the activating group renders the diaryl carbonate more reactive than diphenyl carbonate.

One method for determining whether a certain diaryl carbonate is activated or is not activated is to carry out a model melt transesterification reaction between the particular diaryl carbonate and a phenol such as para—(1,1,3,3-tetramethyl)butyl phenol (and comparing the relative reactivity against diphenyl carbonate). This phenol is preferred because it possesses only one reactive site, possesses a low volatility, and possesses a similar reactivity to bisphenol-A.

The model melt transesterification reaction is carried out at temperatures above the melting points of the particular diaryl carbonate and phenol in the presence of a transesterification catalyst, which is usually an aqueous solution of sodium hydroxide or sodium phenoxide. The concentrations of the transesterification catalyst are at about 0.001 mole percent based on the number of moles of the phenol or diaryl carbonate. Although a desired reaction temperature is 200° C., the choice of reaction conditions as well as catalyst concentration can be adjusted depending on the reactivity and melting points of the reactants to provide a convenient reaction rate. The reaction temperature is preferably maintained below the degradation temperature of the reactants. Sealed tubes can be used if the reaction temperatures cause the reactants to volatilize and affect the reactant molar balance. A determination of an equilibrium concentration of the reactants is accomplished through reaction sampling during the course of the reaction with subsequent analysis of the reaction mixture using well-known detection methods such as HPLC (high pressure liquid chromatography). Particular care needs to be taken so that the reaction does not continue after the sample has been removed from the reaction vessel. This is accomplished by cooling down the sample in an ice bath and by employing a reaction quenching acid, such as acetic acid, in the water phase of the HPLC solvent system. It may also be desirable to introduce the reaction quenching acid directly into the reaction sample in addition to cooling the reaction mixture. A preferred concentration for the reaction quenching acid, e.g., acetic acid in the water phase of the HPLC solvent system, is about 0.05 mole percent. The equilibrium constant is then determined from the concentration of the reactants and product after equilibrium is reached. Equilibrium is assumed to have been reached when the concentration of components in the reaction mixture reach a point of little or no change on sampling of the reaction mixture. The equilibrium constant can be determined from the concentration of the reactants and products by methods well known to those skilled in the art. A diaryl carbonate which possesses a relative equilibrium constant ($K_{diarylcarbonate}/K_{diphenylcarbonate}$) of greater than 1 is considered to possess a greater reactivity than diphenyl carbonate and is a suitable activated aromatic carbonate for use in the present disclosure, whereas a diaryl carbonate which possesses an equilibrium constant of 1 or less is considered to possess the same or have less reactivity than diphenyl carbonate and is considered not to be activated. It is generally preferred to employ an activated aromatic carbonate with very high reactivity compared to diphenyl carbonate when conducting transesterification reactions. Preferred are activated aromatic carbonates with an equilibrium constant greater than at least 1,000 times that of diphenyl carbonate.

The polycarbonates may further comprise structural units derived from at least one endcapping agent not derived from the activated aromatic carbonate. Suitable endcapping agents include phenol, and monoalkyl-substituted or monoaryl-substituted phenols, such as para-cumylphenol, para-cresol, and the like.

The polycarbonates can be prepared by the interfacial process, by using a carbonyl halide as the carbonate source, or by the melt polymerization process by using a diaryl carbonate, or by methods known in the art.

The disclosure is explained in more detail with reference to the following non-limiting Examples, which are only illustrative, but not limitative.

EXAMPLES

Particle size distribution was measured using a Horiba Particle Size Analyzer, Model LA-920 Laser Particle Size Analyzer (LPSA) equipped with a fraction cell holder. LPSA measurements were made using a sample that was dispersed in a dispersant—surfactant mixture and agitated continuously with a magnetic stirrer to obtain a uniform suspension. The analysis was carried out with a relative refractive index of 1.6. The dispersant—surfactant mixture contained 0.1 weight percent of sodium hexametaphosphate, 0.1 weight percent of silicone oil, and 99.8 weight percent of hexane. The resulting mixture was thoroughly mixed using an ultrasonic agitator. In a 50 milliliter vial was placed 0.1 grams of para, para-PPPBP sample and 10 milliliters of the surfactant—dispersant mixture, and the mixture was thoroughly mixed using an ultrasonic agitator for 8 minutes. To measure the particle size distribution of the sample a few drops of the sample, prepared as above was introduced into the fraction cell. The magnetic stirrer in the fraction cell holder was kept "on" throughout the analysis to avoid the sample from settling at the bottom of the fraction cell. All measurements were carried out using a relative refractive index of 1.6. The results are expressed in terms of a mean particle size, and the particle size distribution is given by a median particle size, a mode particle size, and a particle size range, given by the highest and the lowest measured particle size. The values obtained with this method agree well with measurements made using other techniques, such as optical microscopy. Particle size data for the samples of Examples 1 and 2 are shown in Table 1.

Tap density of the samples was measured as follows. An empty vial was filled up the 32.5 cubic centimeter mark with para, para-PPPBP and the weight ($w_1$) of the sample taken was determined. The vial was then dropped from a height of 10 centimeters in a vertical position. This step was repeated for a total of 25 times. The volume ($v_2$) and weight ($w_2$) were recorded. The tap density of the sample was measured from the ratio $w_2/v_2$. Using this procedure, the tap density of the control sample of para, para-PPPBP was measured to be 1.043, and the tap density of a sample of para, para-PPPBP of Example 1 (shown in Table 1 below) having an enhanced mean particle size of about 15 microns was found to be 1.109. This experiment shows that the sample having an enhanced particle size also has a higher tap density.

Example 1

General Procedure for Producing PPPBP Having an Increased Particle Size

One part by weight of PPPBP was mixed with 4 parts by volume of a solvent system comprising water and an organic solvent selected from isopropanol (IPA), and methanol at ambient temperature. The resulting mixture was stirred at a suitable temperature for a suitable period of time. Then the resulting slurry was filtered, washed with water, and dried. The solid material was analyzed for the mean particle size by the procedure described above. Results are shown in Table 1.

The control sample refers to a sample of PPPBP (prepared by reaction of phenolphthalein with aniline in the presence of aniline hydrochloride, followed by dissolution in aqueous sodium hydroxide, acidifying the solution with hydrochloric acid to precipitate the PPPBP solid, washing the solid by stirring with methanol, filtering, and drying) that was used as a feed for the particle size enhancement, and had a mean particle size of 1.7 microns. In Table 1, "ml" stands for milliliters, "Ex. No." stands for Example Number, IPA stands for isopropyl alcohol, and "NA" stands for "not applicable". The mean, median, mode, and particle size range for each example is also shown.

TABLE 1

| Ex. No. | Solvent System composition | | | Temperature (° C.) | Time (hours) | Mean particle size (microns) | Median (microns) | Mode (microns) | Range (microns) |
| | Water (ml) | Methanol (ml) | IPA (ml) | | | | | | |
| --- | --- | --- | --- | --- | --- | --- | --- | --- | --- |
| 1 | 150 | 0 | 150 | 95 | 3 | 16 | 15 | 21 | 1-60 |
| 2 | 100 | 0 | 300 | 95 | 2 | 27.6 | 19.1 | 18.5 | 1-100 |
| Control | NA | NA | NA | NA | NA | 1.7 | 1.6 | 1.8 | 0.3-4 |

The results in Table 1 show that use of water-methanol and water-IPA solvent systems results in an increase in the mean particle size from 1.7 microns in the control sample (feed PPPBP) to greater than 15 microns in Examples 1 and 2.

This written description uses examples to disclose the invention, including the best mode, and also to enable any person skilled in the art to make and use the invention. The patentable scope of the invention is defined by the claims, and may include other examples that occur to those skilled in the art. Such other examples are intented to be within the scope of the claims if they have structural elements that do not differ from the literal language of the claims, or if they include equivalent structural elements with insubstantial differences from the literal languages of the claims.

The invention claimed is:

1. A method for increasing a mean particle size of a 2-hydrocarbyl-3,3-bis(hydroxyaryl)phthalimidine, the method comprising:
   forming a mixture of a 2-hydrocarbyl-3,3-bis(hydroxyaryl)phthalimidine having a mean particle size less than 2 microns and a solvent composition comprising an organic solvent and water, wherein the solvent composition is capable of at least partially dissolving the 2-hydrocarbyl-3,3-bis(hydroxyaryl)phthalimidine;
   forming an adduct of the 2-hydrocarbyl-3,3-bis(hydroxyaryl)phthalimidine; and
   heating the mixture at a temperature and for a time effective to decompose the adduct to form a 2-hydrocarbyl-3,3-bis(hydroxyaryl)phthalimidine product having a mean particle size greater than 5 microns.

2. The method of claim 1, wherein the solvent composition further comprises an acid.

3. The method of claim 2, wherein the solvent composition comprises up to about 1 weight percent of the acid relative to the combined weight of the organic solvent and water.

4. The method of claim 1, wherein the organic solvent is an organic hydroxy compound, an organic ketone compound, an organic amide compound, an organic sulfoxide compound, an organic nitrile compound, an organic amine compound or a combination of at least one of the foregoing compounds.

5. The method of claim 4, wherein the organic solvent is an aliphatic hydroxy compound, an aromatic hydroxy compound, an aliphatic ketone compound, an aliphatic amide compound, an aliphatic amine compound, an aromatic amine compound, an aliphatic sulfoxide compound or a combination of at least one of the foregoing compounds.

6. The method of claim 5, wherein the organic solvent is methanol, ethanol, isopropanol, sec-butanol, phenol, acetone, butanone, formamide, methyl amine, isopropyl amine, dimethyl sulfoxide, aniline, or a combination of at least one of the foregoing compounds.

7. The method of claim 1, wherein the organic solvent is completely miscible with water.

8. The method of claim 1, wherein the 2-hydrocarbyl-3,3-bis(hydroxyaryl)phthalimidine product is 2-phenyl-3,3-bis(4-hydroxyphenyl)phthalimidine.

9. A 2-hydrocarbyl-3,3-bis(hydroxyaryl)phthalimidine product produced in accordance with the method of claim 1.

10. The 2-hydrocarbyl-3,3-bis(hydroxyaryl)phthalimidine product of claim 9, having a mean particle size of greater than 5 microns.

11. A method for increasing a mean particle size of a 2-hydrocarbyl-3,3-bis(hydroxyaryl)phthalimidine compound, the method comprising:
    contacting the 2-hydrocarbyl-3,3-bis(hydroxyaryl)phthalimidine compound having a mean particle size less than 2 microns with a first solvent composition comprising an organic solvent, wherein the solvent composition is capable of at least partly dissolving the 2-hydrocarbyl-3,3-bis(hydroxyaryl)phthalimidine to form a mixture comprising an adduct of 2-hydrocarbyl-3,3-bis(hydroxyaryl)phthalimidine; and
    contacting the mixture with a second solvent comprising water at a temperature and for a time effective to form a 2-hydrocarbyl-3,3-bis(hydroxyaryl)phthalimidine product having a mean particle size greater than 5 microns.

12. The method of claim 11, wherein the first solvent is completely miscible with the second solvent.

13. The method of claim 11, wherein the organic solvent is an organic hydroxy compound, an organic ketone, an organic amide, an organic sulfoxide, an organic nitrile, an organic amine, or a combination of at least one of the foregoing.

14. The method of claim 13, wherein the organic solvent is an aliphatic hydroxy compound, an aromatic hydroxy compound, an aliphatic ketone, an aliphatic amide compound, an aliphatic amine compound, an aromatic amine compound, an aliphatic sulfoxide compound, or a combinations of at least one of the foregoing.

15. The method of claim 11, wherein the organic solvent is methanol, ethanol, isopropanol, sec-butanol, phenol, acetone, butanone, formamide, methyl amine, isopropyl amine, formamide, dimethylsulfoxide, aniline, or a combination of at least one of the foregoing.

16. The method of claim 11, wherein the mean particle size of the 2-hydrocarbyl-3,3-bis(hydroxyaryl)phthalimidine product is 5 microns to 100 microns.

17. The method of claim 11, wherein the second solvent further comprises a water-miscible organic solvent.

18. The method of claim 17, wherein the water-miscible organic solvent is a water-soluble aliphatic alcohol, an aliphatic amine, an aliphatic ketone, an aliphatic amide, an aliphatic nitriles, or a combinations of at least one of the foregoing.

19. The method of claim 11, wherein the second solvent further comprises an acid.

20. A method of making a polycarbonate, the method comprising reacting a aromatic dihydroxy compound mixture comprising a 2-hydrocarbyl-3,3-bis(hydroxyaryl)phthalimidine with a carbonic acid derivative, wherein the 2-hydrocarbyl-3,3-bis(hydroxyaryl)phthalimidine has an average particle size of at least about 5 microns.

21. The method of claim 20, wherein the aromatic dihydroxy compound mixture consists of 2-hydrocarbyl-3,3-bis(hydroxyaryl)phthalimidine, and the 2-hydrocarbyl-3,3-bis(hydroxyaryl)phthalimidine is 2-phenyl-3,3-bis(4-hydroxyphenyl)phthalimidine.

22. The method of claim 21, wherein the carbonic acid derivative is selected from the group consisting of a carbonic acid dihalide, an unactivated carbonic acid diester, an activated carbonic acid diester, and combinations thereof.

23. A method for preparing a 2-hydrocarbyl-3,3-bis(hydroxyaryl)phthalimidine having a mean particle size greater than 5 microns, the method comprising:
    reacting a phenolphthalein compound, with a primary hydrocarbyl amine compound, and an acid catalyst to form a 2-hydrocarbyl-3,3-bis(hydroxyaryl)phthalimidine compound;
    forming a mixture comprising the 2-hydrocarbyl-3,3-bis(hydroxyaryl)phthalimidine compound and a solvent composition comprising at least one organic solvent and water;
    forming an adduct of the 2-hydrocarbyl-3,3-bis(hydroxyaryl)phthalimidine compound; and
    heating the mixture at a temperature and for a time sufficient to decompose the adduct and to form a 2-hydrocarbyl-3,3-bis(hydroxyaryl)phthalimidine product having a mean particle size of greater than 5 microns, wherein the 2-hydrocarbyl-3,3-bis(hydroxyaryl)phthalimidine has a formula:

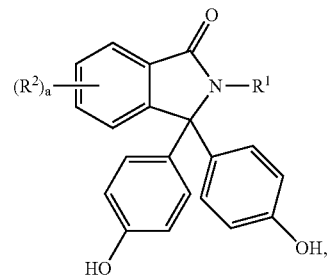

wherein $R^1$ is selected from the group consisting of a hydrogen and a hydrocarbyl group, $R^2$ is selected from the group consisting of a hydrocarbyl group and a halogen; and "a" is 0-4.

24. The method of claim 23, wherein the 2-hydrocarbyl-3,3-bis(hydroxyaryl)phthalimidine is 2-phenyl-3,3-bis(4-hydroxyphenyl)phthalimidine.

* * * * *